United States Patent [19]

Berrehail

[11] Patent Number: 4,836,195
[45] Date of Patent: Jun. 6, 1989

[54] DEVICE FOR ABDUCTION OF UPPER LIMBS

[76] Inventor: Mohamed Berrehail, Chemin de Beausejour, Le Charlaix, 38240 Meylan, France

[21] Appl. No.: 89,043

[22] Filed: Aug. 24, 1987

[51] Int. Cl.$^4$ .............................................. A61F 5/04
[52] U.S. Cl. .................................. 128/83; 128/89 R; 128/77; 128/94
[58] Field of Search ............... 128/77, 83, 84 R, 87 R, 128/87 C, 87 B, 89 R, 94, 75

[56] References Cited

U.S. PATENT DOCUMENTS

| | | | |
|---|---|---|---|
| 1,011,146 | 12/1911 | Baxter | 128/94 |
| 1,257,297 | 2/1918 | Brown | 128/88 X |
| 1,639,815 | 8/1927 | Siebrandt | 128/88 |
| 1,653,601 | 12/1927 | Foulke | 128/88 |
| 2,191,283 | 2/1940 | Longfellow | 128/88 |
| 2,859,746 | 11/1958 | Roberson | 128/87 R |
| 3,215,138 | 11/1965 | Groesbeck | 128/94 |
| 3,780,729 | 12/1973 | Garnett | 128/94 |
| 3,952,733 | 4/1976 | Williams | 128/83 X |
| 4,055,171 | 10/1977 | Ries | 128/94 X |
| 4,143,654 | 3/1979 | Sherman | 128/87 R |
| 4,180,870 | 1/1980 | Radulovic | 128/77 X |
| 4,417,569 | 11/1983 | Brudny | 128/77 |
| 4,651,719 | 3/1987 | Funk et al. | 128/77 X |

FOREIGN PATENT DOCUMENTS

| | | |
|---|---|---|
| 891007 | 9/1953 | Fed. Rep. of Germany . |
| 1147711 | 4/1963 | Fed. Rep. of Germany . |
| 752041 | 9/1933 | France . |

Primary Examiner—Robert A. Hafer
Assistant Examiner—Kevin G. Rooney
Attorney, Agent, or Firm—Browdy and Neimark

[57] ABSTRACT

A device for abduction of the upper limbs of a patient comprising a belt and at least one plate made of a rigid material which is capable of being deformed. A belt is provided to encompass the trunk of the patient and is equipped with at least one pocket which is intended to receive the crosswise segment of the at least one rigid yet deformable plate. The vertical segment or segments of the plate are provided to hold the arm and the forearm of the patient in the desired position, and means are provided for supporting the base of the deformed portion of the plate and assuring better distribution of weight.

19 Claims, 6 Drawing Sheets

DEVICE FOR ABDUCTION OF UPPER LIMBS

FIELD OF THE INVENTION

The present invention relates to a device for abduction of the upper limbs.

BACKGROUND OF THE INVENTION

It is quite often necessary, in the treatment of shoulder injuries and operations, to keep the shoulder in a position that is spaced apart with respect to the median plane of the body, with elevation of the associated arm.

However, devices proposed for this purpose up to now have not been entirely satisfactory.

The disadvantages of plaster thoracobrachial casts are well known; they are fixed, heavy devices, and making them is a long and complicated process. Also, to avoid any breakage, a rod for supporting the mass of the plaster must be integrated with it.

It is no longer entirely satisfactory to replace the plaster, which is a heavy and relatively fragil material, with synthetic thermoformable materials that are lighter and stronger, especially because of the cost price of the fitting process, since the basic material is expensive; all the constituent parts of the device must be molded while hot, piece by piece, before being soldered, again piece by piece and with heat. Fitting of the cast is laborious, and adjusting it by cutting off excess material once the device is in place produces sharp edges. Finally, as in the case of plaster, the device can be used only once.

Metal thoracobrachial devices are also expensive and heavy, since all the parts are made to measure and are articulated, which necessitates many screws and bolts and requires major adjustment.

Finally, in certain cases, simple supports of foam rubber or expanded plastic held in place with a bandage are used; however, in this case there is not always enough support and above all, as with all the other devices described above, it is not easy to vary the angle of abduction and keep it in the desired position for the required duration of treatment.

It will be appreciated that there is a need for a lighter abduction device that is easily adjusted on the patient, even by the attending physician, to attain the exact solution sought to the problem presented by the particular injury, whether it be dislocation of the shoulder, fracture of the upper end of the humerus, or any other surgery or post-operative treatment of the shoulder.

SUMMARY OF THE INVENTION

It is accordingly the object of the present invention to furnish a device that overcomes the disadvantages of the prior art while making it possible to obtain an angle of abduction, forward and backward displacement of the upper limb as desired by the physician and to vary the flexion of the forearm on the arm at will and to keep this position firmly. This device is light; it can be put in place easily and can be taken off at any time to permit intermittent local intervention. Moreover, it has the major advantage of being supplied in the form of elements that can easily be assembled by the physician and adapted to all patients.

The device for abduction of the upper limbs according to the invention substantially comprises a basic belt and at least one plate made of a rigid material capable of being deformed. The belt is provided to encompass the trunk and is equipped with at least one pocket, which is intended to receive the crosswise segment of the at least one rigid, yet deformable plate; the vertical segment or segments of the plate are provided to hold the arm and the forearm in the desired position, and means are provided for supporting the base of the deformed portion of the plate and assuring better distribution of weight, since all these elements are provided to be assembled and adapted by the physician himself.

In a first embodiment, the plate or plates of rigid deformable material is generally in the shape of a T.

In a second embodiment, the plate of semi-rigid deformable material is in the general shape of a U, the crosswise segment of the U being provided to comprise the base of the device and the vertical arms being provided to hold the arm and forearm in the desired position.

In a third embodiment, the plate of semi-rigid deformable material is in the general shape of a T, the vertical segment of which is elongated laterally with a horizontal segment disposed substantially parallel to the crosswise segment of the T.

In a preferred embodiment of the invention, means are provided for joining together the arm and the forearm, respectively, to the deformed portion of the plates.

Means are advantageously provided for receiving the ends of the deformed portions of two plates.

The rigid material that is capable of being deformed is preferably selected from among any moldable elements, such as metals and metal alloys and in particular aluminum.

BRIEF DESCRIPTION OF THE DRAWINGS

The present invention will be better understood and its advantages will become more apparent from the ensuing description of three embodiments of the abduction device according to the invention, taken in conjunction with the schematic drawings, in which.

DESCRIPTION OF THE PREFERRED EMBODIMENTS

The drawing figures show the device 1 according to the invention, the basic belt 2, the deformable plate 3, and the means 4 provided for supporting the base of the deformable portion of the plate.

The abduction device 1 according to the invention substantially comprises the elements described below, which are provided for being assembled at the time of use.

A basic belt 2 is provided to encompass the trunk of the patient. This is a band or tape made of any relatively flexible known material such as a woven fabric or elastic knit, preferably reinforced with elastic foam rubber or expanded plastic. This belt is equipped with closure and locking means 5 that enable adjusting the belt 2 to the waist of the patient. These means may be any standard means, such as buckles, snaps, laces, or preferably interlocking female and male velour-type elements such as those sold under the tradename "VELCRO".

The belt 2 also equipped with a 2-ply segment 6 that forms a pocket capable of receiving the deformable plate or plates 3. This pocket may occupy all or part of the surface of the band comprising the belt 2.

Similarly, and without departing from the scope of the invention, it can be separated into separate compartments, each of which receives one of the aforementioned plates.

Preferably, and for the sake of both better hygiene and increased comfort, the plate or plates 3 are accommodated in a removable cover 7 of knitted or woven fabric, optioally padded with expanded plastic. Closing means 8 are provided for closing the cover 7 and opening it again at will, in particular for removing the plate in order to wash the cover. These closing means are selected from among standard means, such as zippers, Velcro-type elements, and so forth.

At the moment when the device is put in place, the vertical segment or segments of the deformable plates are curved along the angle intended for keeping the arm and forearm in the desired abduction position, as will be explained below.

Means 4 are also provided for supporting the lower portion of the curve of the deformable plates once they are in place and for enabling better distribution of the weight to the pelvis. In the embodiment shown in the drawing, this is a shoulder strap comprising a band of woven or knitted material, also padded with foam rubber or expanded plastic; the portion that is intended to be in direct contact with the skin is preferably made of cotton, for the sake of patient comfort. The strap is provided with means capable of assuring its adjustment, closure and retention in the desired position, such as the buckle 9. Velcro-type elements are provided at 10 for fixation on a complementary Velcro-type element disposed on the folded-over portion.

Various embodiments of the device according to the invention will now be described in greater detail.

The plates 3, comprising one of the essential elements of the device, are made of a semi-rigid material that can be deformed so as to assume and maintain a selected angle of curvature. Among the many materials suitable for this purpose, aluminum or aluminum-based alloys are highly suitable, since the thickness of the plate is approximately 2.5 mm. The crosswise segment of each of the plates 3 is provided for accommodation within the pocket or pockets made in the belt 2. It is also given a curvature by bending so as to adapt to the shape of the patient's trunk.

The first embodiment will now be described, referring to FIGS. 1–4.

Figure 1:
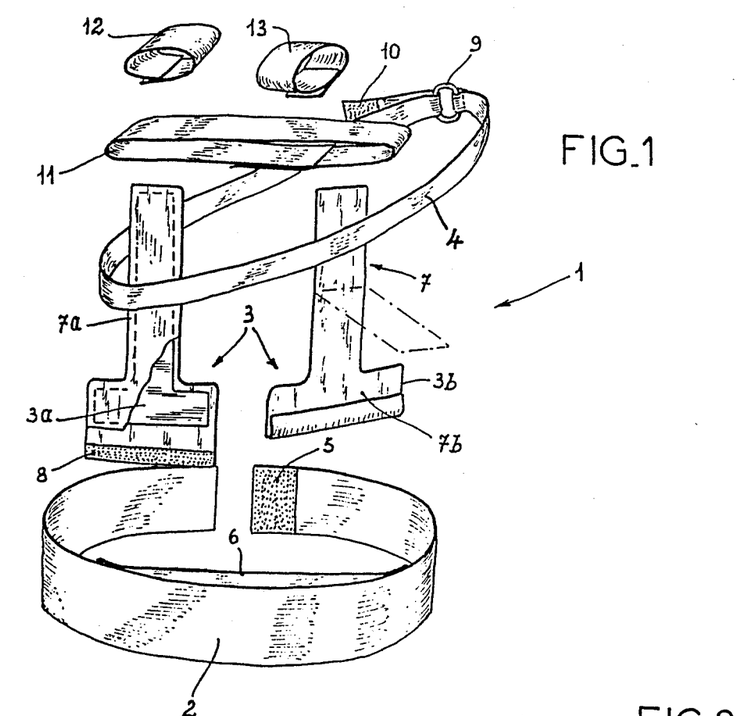
FIG. 1 is a perspective view of all the constituent elements of a first embodiment of the device.

The device includes two deformable plates 3a, 3b having the general shape of a T.

The abduction device according to the invention also includes a continuous band 11 provided for joining the upper portion of the plates 3a, 3b as well as straps 12, 13 provided for joining and immobilizing the arm and forearm, respectively, to the bent portion of the plates 3 and to the band 11, which serves to provide horizontal support to the forearm. The fastening straps 12 and 13 are made of flexible elastic material (woven or knitted), optionally reinforced with foam rubber or expanded plastic; the fastening straps 12 and 13 are also equipped with Velcro-type means so that they can be easily put in place and to assure their closure and later reopening.

Figure 2:
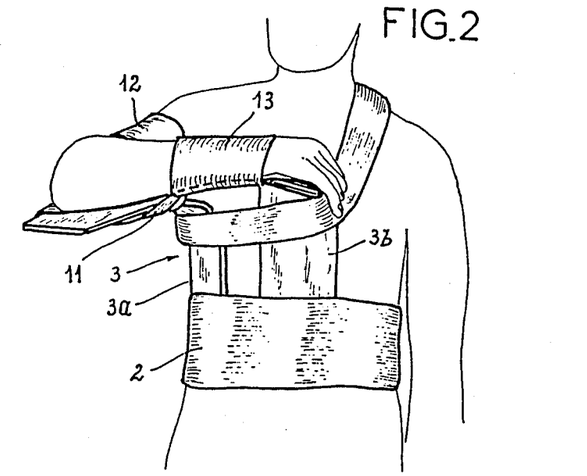
FIG. 2 is a front view of the device of FIG. 1, in place on a patient, for a particular position of the upper limb with abduction of approximately 90°.
Figure 3:
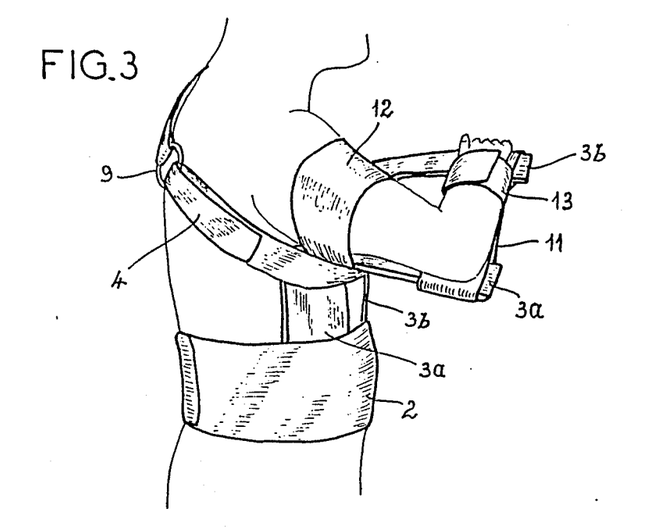
FIG. 3 is a side view of the device shown in FIG. 2.

FIGS. 2 and 3 show the abduction device for the upper limbs according to the invention put in place for a given position of the arm and forearm (abduction of approximately 90°).

The crosswise portions of the plates 3a and 3b, once they are in place in the removable covers 7a and 7b are introduced into the pockets 6 made in the belt 2 and are curved so that they adapt to the shape of thef trunk; the belt is adjusted to the waist of the wearer with the aid of the closing and locking elements 5. The plate 3a is then curved by the physician to the angle he specifies, so that it supports the arm; similarly, after curvature to the desired position, the plate 3b supports the forearm. The band 11 is then put in place to keep the folded top of the two plates 3a, 3b in a predetermined relative position; it likewise serves to support the forearm. Then the arm and the upper portion of the plate 3a are joined with the aid of the fastening strap 12, and the same is done for the fastening strap 13 to join the wrist and the upper portion of thfe plate 3b.

Finally, the shoulder strap 4 is put in place, enabling better destribution of the weight of the device.

Figure 4:
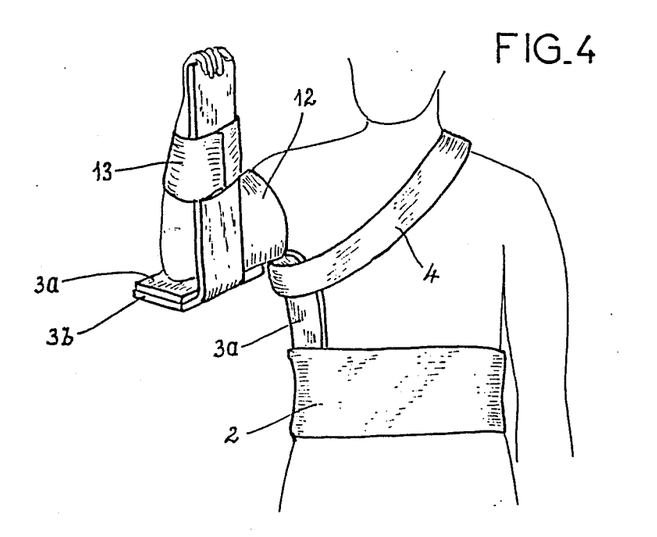
FIG. 4 is a front view of the device of FIG. 1 for an abduction and external rotation position of the upper limb.

The device can also be put in place in the position shown in FIG. 4. In this case, only the plate 3a, lined with its protective cover, is placed in the pocket made in the belt 2, and the plate 3b, likewise lined with its protective cover, is folded to the level of its crosswise portion and is used in conjunction with the upper portion of the plate 3a to enable keeping the forearm and the arm in the abduction and external rotation position shown in this drawing figure.

This position is obtained by a judicious placement fo the plate 3b under the plate 3a; these plates, lined with their covers, can be joined together either by Velcro-type means or via fastening straps such as those shown at 12 and 13.

In the embodiment shown in FIGS. 2–7, the same elements are identified by the same reference numerals.

Figure 5:
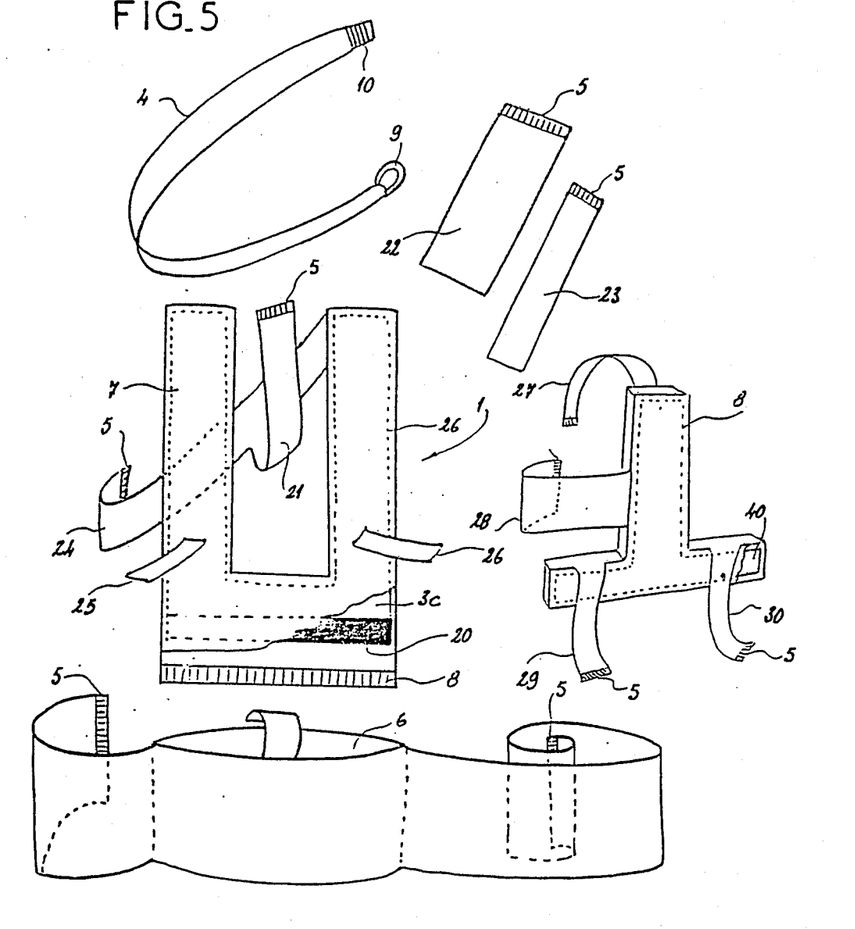
FIG. 5 is a perspective view of all the constituent elements of a second embodiment of the apparatus according to the invention.

In this case, the deformable plate 3c has the general shape of a U including two vertical segments joined at their base with a crosswise segment provided for being housing in the pocket 6 made in the belt 2. A roll of padding 20, for example of natural rubber, is fixed to the lower edge of the crosswise segment of the U-shaped plate, to provide an element for protection from the sharp edge of this plate.

Various fastening straps 21, 22, 23, 24, 25, 26 are also provided to assure correct placement and maintenance of the device in position on the patient.

Each of these fastening straps is equipped with closure and locking means 5.

These means are joined to the cover 7 by sewing; they can also be detachable and equiped with Velcro-type means capable of cooperating with the "VELCRO" surface of the cover 7. The means 21, 22, 23, 24 are intended for keeping the upper limb on the U-shaped element. The means 25 and 26 are intended to assure fixation of the cover 7 on the belt 2 to prevent its slipping down. Finally, the belt 4 passes behind the head of the patient and holds the two vertical segments of the U-shaped element in place around the neck.

Figure 6:
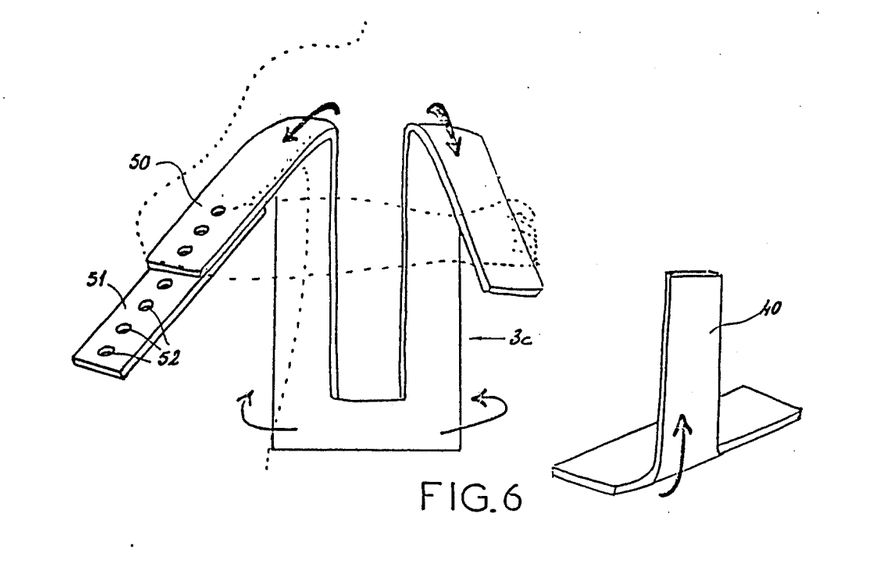
FIG. 6 is an exploded perspective view of the deformable plate of FIG. 5 for an abduction position of the upper limb of approximately 90°.
Figure 7:
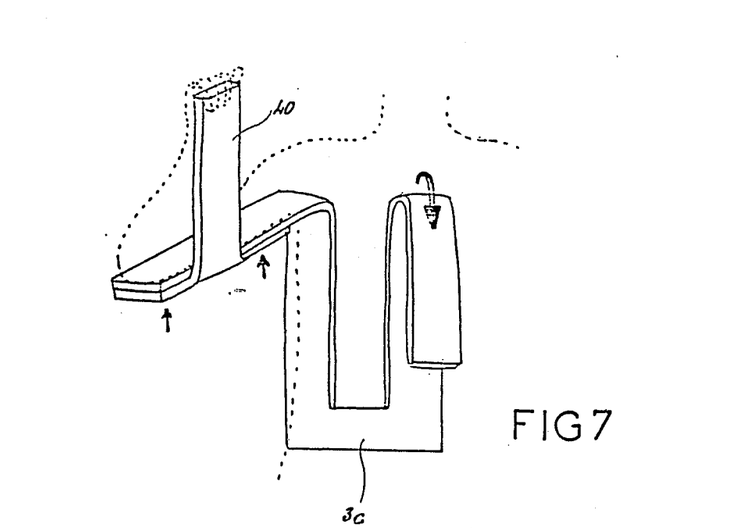
FIG. 7 is a front view of the deformable plate of FIG. 5 for an abduction and external rotation position of the upper limb.

In FIGS. 6 and 7, which show the manner of placement of the device, the plate 3c is shown without the cover 2, for the sake of better understanding.

An accessory of rigid deformable material in the shape of a T, identified by reference numeral 40, can be associated with the apparatus as shown in FIG. 6, and is also placed in a cover 8 provided with fastening straps 27, 28, 29, 30, and the crosswise segment of which is provided for cooperation with one of the vertical segments of the U-shaped element for fixation of the upper limb in abduction and external rotation.

The placement of the device on the patient will now be described.

The various elements (U-shaped plate 3c, accessory 40) are inserted into their respective covers 7, 8.

This abduction device serves to immobilize a certain number of injuries to the shoulder and upper limb generally in a position of simple abduction or of external rotation and abduction.

To obtain simple abduction, the device is first bent by the physician at the level of the vertical segments (FIG. 6), prior to being applied to the patient. The physician deforms the crosswise segment to lend it a curvature that will adapt to the contours of the patient's abdomen. The device is applied underneath the upper limb of the patient. The various closures (fastening straps, belts, shoulder straps) are then adjusted.

To obtain external rotation and abduction of the upper limb, which is particularly necessary post-operatively after shoulder surgery, the accessory 40 (FIG. 6) is then bent.

This accessory 40 is then placed under one of the already-bent vertical segments of thfe U-shaped element 3c. It is fixed by the fastening straps 29 and 30 on the vertical segment of the U-shaped element and also on the forearm and hand of the patient by the fastening straps 28 and 27.

Finally, in the case where it will be necessary to exert traction of some kind on the bent arm, the vertical segments of the U are provided with a series of threaded holes 50. A strip 51 also including a series of threaded holes 52, corresponding to the series of holes 50, is also provided; certain of the holes 50 and 52 can be made to coincide and the strip 51 can be affixed by screws to one of the vertical segments, as shown in FIG. 6. Thus a means is available with which traction can optionally be exerted on the arm, since the strip 51 is also lined with a protective cover that is elongated by a pullable tab (not shown).

Finally, in the embodiment shown in FIGS. 8–11, the plate 3d of rigid deformable material is in the shape of a T, the vertical segment of which is elongated laterally to its opposite end to the crosswise segment with a horizontal segment that is substantially parallel to this crosswise segment.

Figure 8:
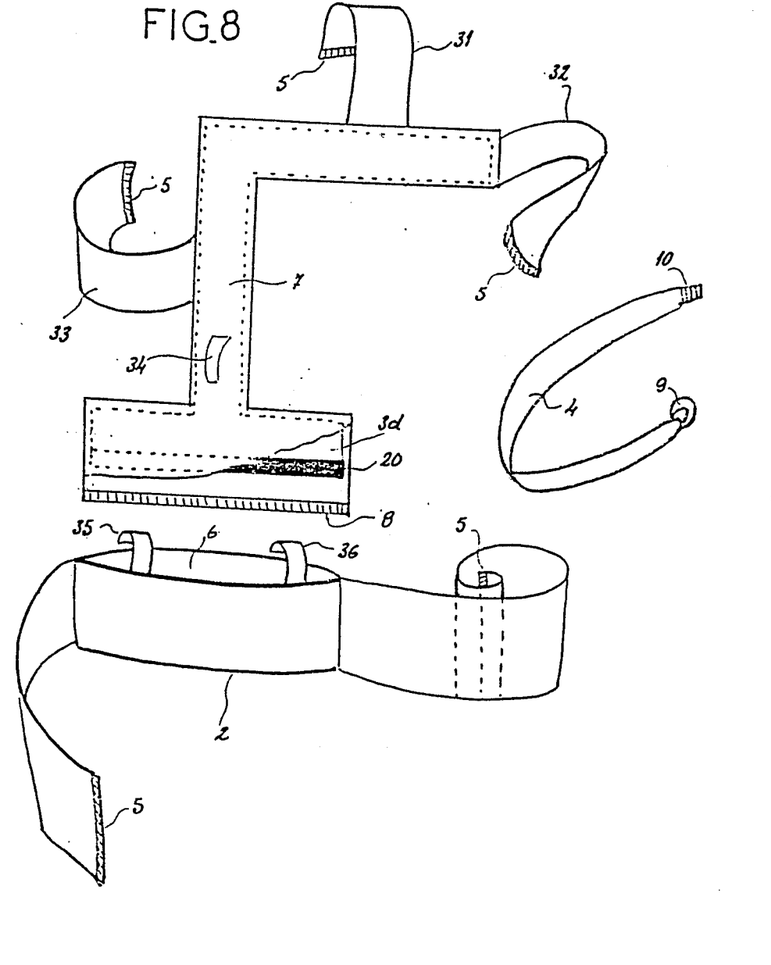
FIG. 8 is a perspective view of all the constituent elements of a third embodiment of the device according to the invention.
Figure 9:
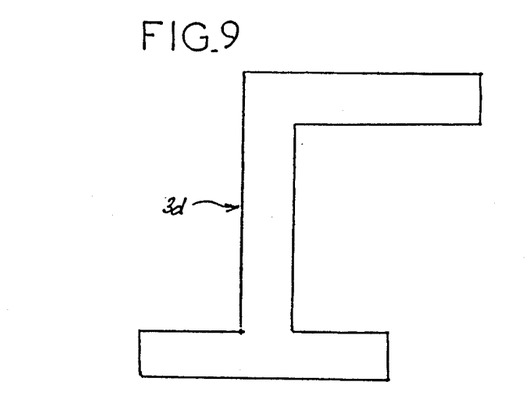
FIG. 9 is a flat view of the deformable plate of FIG. 8.

The cover 7 provided for receiving the plate 3d is equipped with attachment and fastening straps 31, 32, 33, 34; the belt 2 is also equipped with supplementary fastening straps 35 and 36 intended for locking the crosswise segment of the T-shaped plate 3d in position.

The applications of the device shown in FIGS. 8–11 are substantially the same as those of the device shown in FIGS. 1–7.

Placement of both devices on a patient is virtually identical.

Figure 10:
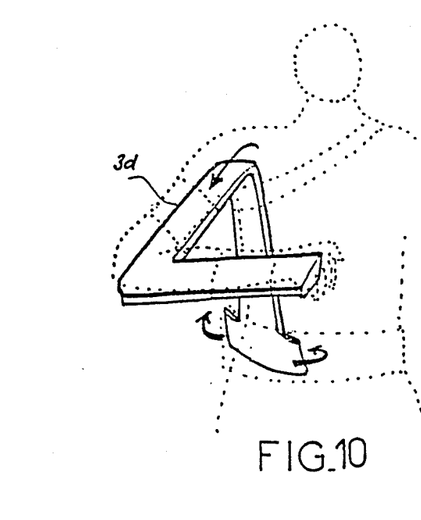
FIG. 10 is a front view of the deformable plate of FIG. 9 for an abduction position of approximately 90° of the upper limb.

For simple abduction of the upper limb, the physician bends the vertical segment and the crosswise segment sufficiently (FIG. 10).

Figure 11:
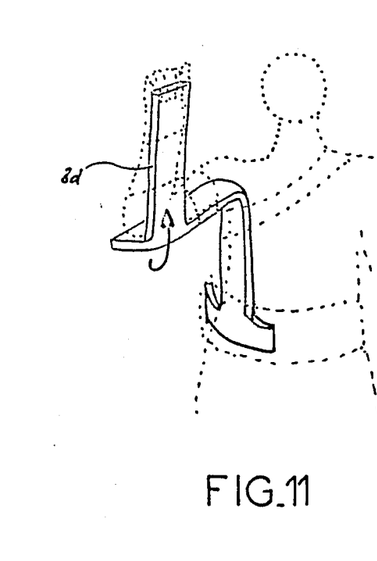
FIG. 11 is a front view of the deformable plate of FIG. 9 for an abduction and external rotation position of the upper limb.

For obtaining external rotation abduction, the physician completes the bending at the level of the lateral segment (FIG. 11).

The various covers 7, 8, the belt 2 and the various fastening straps are advantageously made of a synthetic alveolar material, or expanded plastic, approximately 4–10 mm in thickness, covered on one surface –the surface intended to be in contact with the patient's body –with cotton or any non-allergenic fabric and on the other surface with a velour-type fabric or raised mesh capable of comprising the female portion of Velcro-type fastening systems, the male portions preferably being those shown in the drawing at reference numeral 5.

The importance of the present abduction device according to the invention for the physician will be appreciated. In effect, the physician now has a device for abduction and external rotation of the shoulder which is especially efficacious, and which is in the form of separate elements that the physician can easily assemble when he desires it and can adapt at will depending on the treatment desired.

Once assembled, these elements assure immobilization and comfortable restraint of the shoulder and the upper limb. They can easily be taken off to permit intermittent local intervention, for instance for washing, bandaging, removal of sutures, or topical application of medicine, and can then be put back in place. Finally, and this is quite important from the standpoint of hygiene, all the external parts of the device are made of washable elements, the portions being in contact with the skin preferably being made of cotton.

It should also be noted that the abduction device according to the invention can be used at will on the left or right, and that it can easily be adapted to any body shape. Finally, it constitutes a valuable aid in all cases of emergency trauma, because it is so easy to put into place and adapt to the patient's body.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology employed herein is for the purpose of description and not of limitation.

What is claimed is:

1. A device for abduction of an upper limb which supports both the upper arm and the forearm which supports of a patient comprising:
   a belt for surrounding the trunk of the patient;

at least one unitary plate, initially of generally planar form, made of a semi-rigid material capable of being deformed for maintaining an upper limb in a desired position of abduction, each plate having a base portion which is adapted to lie against the trunk of the patient, and an elongated portion adapted to extend along the trunk of the patient in a form-fitting manner and being connected to said base portion substantially perpendicular thereto, each elongated portion being adapted to be deformed so as to form an angle of approximately 90° with respect to the trunk of the patient and to extend outwardly from the trunk of the patient for supporting a portion of the upper limb;

pocket means for supporting said base portion of said at least one plate disposed on an inside surface of said belt.

2. The device according to claim 1 further comprising strap means extending around the neck of the patient and passing under the deformed unitary portion of said at least one plate for supporting said at least one plate from being further deformed by the upper limb.

3. The device according to claim 1, wherein said at least one plate has a generally T shape.

4. The device according to claim 1, wherein said at least one plate of rigid deformable material is generally U-shaped, having a crosswise segment and two vertical segments, the crosswise segment of the U being provided to form the base of the device, and the vertical segments being provided to keep an arm and a forearm of the patient in the desired position.

5. The device according to claim 4, further comprising an accessory of rigid deformable material being generally T-shaped and having a crosswise segment which cooperates with a vertical segment of the U-shaped crosswise segment of said at least one plate for fixation of the arm of the patient in abduction and external rotation when the device is worn.

6. The device according to claim 1, wherein said at least one plate of rigid deformable material is generally T-shaped having a vertical segment and a crosswise segment, said vertical segment being laterally extended by a horizontal segment disposed substantially parallel to the crosswise segment of the T.

7. The device according to claim 1, wherein the rigid material capable of being deformed is selected from the group consisting of moldable materials.

8. The device according to claim 7, wherein the moldable materials are selected from the group consisting of metals and metal alloys.

9. The device according to claim 8, wherein the metal is aluminum.

10. The device according to claim 1, further comprising at least one detachable cover for covering said at least one rigid deformable plate, said at least one detachable cover being made of washable material and being equipped with means for closure and locking, the means for closure and locking being equipped with fastening means.

11. The device according to claim 1, further comprising fastening means for assuring the proper placement and maintenance in position on the patient.

12. The device according to claim 1, further comprising means for joining the arm and forearm of the patient, respectively, to the deformed portion of the at least one plate.

13. The device according to claim 1, further comprising means for joining the ends of the deformed portions of the at least one plate.

14. The device according to claim 1, wherein said at least one deformable plate comprises a plurality of deformable plates and further comprising joining means for making the plurality of deformable plates cooperate with one another.

15. The device according to claim 12, wherein said means for joining comprise VELCRO-type strips.

16. The device according to claim 13, wherein said means for joining comprise VELCRO-type strips.

17. The device according to claim 14, wherein said means for joining comprise VELCRO-type strips.

18. A device for abduction of an upper limb which support both the upper arm and the forearm of a patient comprising:

support means for surrounding the trunk of the patient;

at least one semi-rigid, deformable unitary plate for maintaining an upper limb in a desired position of abduction, each plate having a base portion which is adapted to lie against the trunk of the patient and an elongated portion adapted to extend along the trunk of the patient in a form-fitting manner and being connected to said base portion substantially perpendicularly with respect thereto and adapted to be deformed so as to adapt to the trunk of the patient and form an angle extending outwardly with respect to the trunk of the patient for supporting a portion of the upper limb;

pocket means for supporting said base portion of said at least one plate disposed on an inside surface of said support means; and strap mean adapted to extend around the neck of the patient and pass under said deformed elongated portion of said at least one plate for preventing said at least one plate from being further deformed by the upper limb.

19. The device according to claim 18, wherein said at least one plate comprises a plurality of plates adapted to cooperate with one another to maintain the limb in the desired position of abduction and further comprising joining means for removably connecting said plurality of plates with one another.

* * * * *